United States Patent
Kobayashi et al.

(10) Patent No.: US 7,919,432 B2
(45) Date of Patent: Apr. 5, 2011

(54) ADSORBENT, ADSORPTION APPARATUS, AND METHOD FOR MANUFACTURING THE ADSORPTION APPARATUS

(75) Inventors: Shintaro Kobayashi, Tokyo (JP); Tsuneo Okuyama, Kanagawa (JP)

(73) Assignees: Hoya Corporation, Tokyo (JP); Tsuneo Okuyama, Kanagawa (JP)

( * ) Notice: Subject to any disclaimer, the term of this patent is extended or adjusted under 35 U.S.C. 154(b) by 1011 days.

(21) Appl. No.: 10/560,077

(22) PCT Filed: Jun. 9, 2004

(86) PCT No.: PCT/JP2004/008364
§ 371 (c)(1),
(2), (4) Date: May 15, 2006

(87) PCT Pub. No.: WO2004/108272
PCT Pub. Date: Dec. 16, 2004

(65) Prior Publication Data
US 2007/0181478 A1 Aug. 9, 2007

(30) Foreign Application Priority Data
Jun. 9, 2003 (JP) ................. 2003-164336

(51) Int. Cl.
*B01D 15/20* (2006.01)
*B01D 11/02* (2006.01)
*C01F 11/02* (2006.01)
*B01J 20/04* (2006.01)
*C02F 1/42* (2006.01)

(52) U.S. Cl. ............. 502/406; 210/198.2; 210/660; 210/679; 423/139; 423/308

(58) Field of Classification Search ............. 502/406; 96/101, 118, 120, 372; 73/23.35, 23.39; 210/198.1, 198.3, 681, 688, 660, 679, 198.2; 423/139, 157, 308
See application file for complete search history.

(56) References Cited

U.S. PATENT DOCUMENTS
4,781,904 A 11/1988 Tagaya et al.
5,651,884 A * 7/1997 Ichitsuka et al. ......... 210/198.2

FOREIGN PATENT DOCUMENTS
EP 0320849 6/1989
(Continued)

OTHER PUBLICATIONS
Lennart et al. Isolation of phosphoproteins by immobilizing metal (Fe3+) Affinity Chromatography, 1986, Analytical Biochemistry 154, 250-254.*
(Continued)

*Primary Examiner* — Wayne Langel
*Assistant Examiner* — Syed Iqbal
(74) *Attorney, Agent, or Firm* — Greenblum & Bernstein, PLC (57) ABSTRACT

In an adsorbent of the present invention, at least a surface and its vicinity thereof is composed of an apatite represented by the formula $Ca_{10}(PO_4)_6((OH)_{1-x}A_x)_2$, where A represents a halogen element and $0 \leq x \leq 1$, and a phosphate group contained in the apatite is bonded to a trivalent metal ion. Further, preferably, the trivalent metal ion is $Fe^{3+}$. According to the present invention, it is possible to provide an adsorbent capable of specifically adsorbing an object compound, an adsorption apparatus capable of separating and purifying the object compound easily and reliably, and a method capable of manufacturing such an adsorption apparatus easily in a short time.

9 Claims, 4 Drawing Sheets

FOREIGN PATENT DOCUMENTS

| | | |
|---|---|---|
| JP | 01-155263 | 6/1989 |
| JP | 01-297553 | 11/1989 |
| JP | 02-237639 | 9/1990 |
| JP | 03-016906 | 1/1991 |
| JP | 07-096175 | 4/1995 |
| JP | 09-175805 | 7/1997 |
| JP | 10-118167 | 5/1998 |
| JP | 10118167 A * | 5/1998 |

OTHER PUBLICATIONS

English language Abstract of JP 10-118167.
English language Abstract of JP 07-096175.
English language Abstract of JP 03-016906.
English language Abstract of JP 02-237639.
English language Abstract of JP 01-297553.
English language Abstract of JP 01-155263.
English language Abstract of JP 09-175805.
Andersson et al., "Isolation of Phosphoproteins by Immobilized Metal ($Fe^{3+}$) Affinity Chromatography," Analytical Biochemistry, vol. 154, pp. 250-254 (1986).
Nordstrom et al., "Generation of a new protein purification matrix by loading ceramic hydroxyapatite with metal ions—demonstration with poly-histidine tagged green fluorescent protein," Journal of Biotechnology, vol. 69, pp. 125-133 (1999).
T. Nordström et al., Journal of Biotechnology, vol. 69, 1999, pp. 125-133.
M. Wakamura et al., Colloids and Surfaces A: Physicochemical and Engineering Aspects, vol. 164, 2000, pp. 297-305.
L. Andersson et al., Analytical Biochemistry, vol. 154, 1986, pp. 250-254.

* cited by examiner

ADSORBENT, ADSORPTION APPARATUS, AND METHOD FOR MANUFACTURING THE ADSORPTION APPARATUS

TECHNICAL FIELD

The present invention relates to an adsorbent, an adsorption apparatus, and a method for manufacturing the adsorption apparatus.

BACKGROUND ART

In the field of protein research, for the analysis of protein structure and function, a large amount of protein is expressed using cDNA, and the thus obtained recombinant protein is separated and purified.

Proteins translated from genes undergo various posttranslational modifications such as phosphorylation and glycosylation to regulate the function thereof. Such posttranslational modifications are involved in intracellular communication, cell-cycle regulation, metabolic control, and the like, and therefore are important cell regulatory mechanisms. In order to research such mechanisms of protein regulation, there is a demand for development of means for separating a non-modified protein and a modified protein from one another for purification.

Meanwhile, hydroxyapatite has excellent biocompatibility, and has been heretofore widely used as an adsorbent in a column (that is, in an adsorption apparatus) for liquid chromatography to adsorb and separate a protein etc (see, for example, U.S. Pat. No. 4,781,904).

However, an adsorbent made of hydroxyapatite non-specifically adsorbs various proteins, and therefore there is a problem that it is difficult to allow such an adsorbent to selectively adsorb a specific protein. For this reason, such a conventional adsorbent made of hydroxyapatite is not suitable for use in separation of a non-modified protein and a modified protein from one another for purification.

DISCLOSURE OF THE INVENTION

In view of the above problem, it is an object of the present invention to provide an adsorbent capable of specifically adsorbing an object compound, an adsorption apparatus capable of easily and reliably separating and purifying the object compound, and a method capable of easily manufacturing such an adsorption apparatus in a short time.

In order to achieve the above object, the present invention is directed to an adsorbent. The adsorbent comprises an apatite which forms at least the surface and its vicinity of the adsorbent and is represented by the formula $Ca_{10}(PO_4)_6((OH)_{1-x}A_x)_2$, where A represents a halogen element and $0 \leq x \leq 1$, and a trivalent metal ion bonded to a phosphate group contained in the apatite.

The adsorbent having such a structure can specifically adsorb a compound (an object compound) having a portion capable of bonding with a high affinity (that is, with a high bonding force) to a trivalent metal ion.

In the adsorbent according to the present invention, it is preferred that the trivalent metal ion is $Fe^{3+}$. This is because $Fe^{3+}$ has a very high bonding ability to a phosphate group (that is, $Fe^{3+}$ has a very high affinity for a phosphate group).

Further, it is preferred that the amount of the trivalent metal ion to be bonded to the apatite is in the range of 0.1 to 100 mg per gram of the apatite. By setting the amount of the trivalent metal ion to be bonded to the apatite to a value within the above range, it is possible for the adsorbent to have a very high ability to specifically adsorb an object compound.

Further, the adsorbent according to the present invention is suitable for adsorbing a compound having a phosphate group. This is because the phosphate group of such a compound forms a coordinate bond with a trivalent metal ion (that is, chelation), and therefore a compound having a phosphate group is particularly firmly adsorbed to the adsorbent through the coordinate bond.

In this case, it is preferred that the compound is a phosphorylated protein. The phosphorylated protein is adsorbed with a very high selectivity to the adsorbent according to the present invention because protein itself is highly adsorptive to an apatite.

Further, in the adsorbent according to the present invention, it is preferred that the A is a fluorine element. Generally, a halide ion can enhance the bonding force between elements (ions) constituting the apatite. In particular, since a fluorine element ion has a higher electronegativity as compared to other halide ions, it is possible to further improve the durability of the apatite (that is, the adsorbent) as well as the resistance to solvents thereof (that is, the adsorbent).

Further, in the adsorbent according to the present invention, it is preferred that the "x" in the formula is in the range of 0.3 to 1. This is because if the "x" is too small, there is a case that it is not possible to improve the durability and resistance to solvents of the adsorbent sufficiently depending on the kind of halogen element A used.

Another aspect of the present invention is directed to an adsorption apparatus comprising a column which has an adsorbent filling space filled with the adsorbent described above. According to such an adsorption apparatus, it is possible to separate and purify a compound (an object compound) comprising a portion having a high affinity (that is, a high bonding force) for the trivalent metal easily and reliably. Namely, it is possible to collect a highly-pure compound comprising a portion having a high affinity for the trivalent metal ion in good yield.

In this case, it is preferred that the adsorbent filling space is substantially fully filled with the adsorbent. By doing so, it is possible to further enhance the ability to separate and purify the object compound.

Further, in the adsorption apparatus according to the present invention, it is preferred that all the adsorbent contained in the adsorbent filling space has substantially the same composition. This makes it possible for the adsorption apparatus to have a particularly high ability to separate and purify the object compound.

Further, in the adsorption apparatus according to the present invention, it is preferred that the adsorbent has a particulate form. By allowing the adsorbent to have a particulate form, it is possible to increase the surface area of the adsorbent, thereby further increasing the amount of the object compound to be adsorbed to the adsorbent.

Further, in the adsorption apparatus according to the present invention, it is preferred that the average particle size of particles of the adsorbent is in the range of 0.5 to 100 μm. By using the adsorbent having such an average particle size, in a case where the adsorption apparatus has a filter member, it is possible to allow the adsorbent to have a sufficient surface area while preventing clogging of the filter member reliably.

The other aspect of the present invention is directed to a method for manufacturing an adsorption apparatus, wherein a solution containing a trivalent metal ion is passed through an adsorbent filling space of a column filled with an apatite represented by the formula $Ca_{10}(PO_4)_6((OH)_{1-x}A_x)_2$, where A represents a halogen element and $0 \leq x \leq 1$, so that a phosphate group contained in the apatite is bonded to the trivalent metal ion. According to such a method, it is possible to manufacture the adsorption apparatus easily in a short period of time.

In this case, it is preferred that the amount of the trivalent metal ion contained in 1 L of the solution is in the range of 1 to 50 mol per mol of the apatite. This makes it possible to efficiently bond the trivalent metal ion to a phosphate group contained in the apatite.

Further, in the method for manufacturing an adsorption apparatus according to the present invention, it is preferred that the total amount of the solution containing the trivalent metal ion to be passed through the adsorbent filing space is in the range of 1 to 50 mL. This also makes it possible to efficiently bond the trivalent metal ion to a phosphate group contained in the apatite.

Further, in the method for manufacturing an adsorption apparatus according to the present invention, it is preferred that the flow rate of the solution containing the trivalent metal ion is in the range of 0.1 to 10 mL/min. This also makes it possible to efficiently bond the trivalent metal ion to a phosphate group contained in the apatite.

These and other objects, structures and results of the present invention will be apparent more clearly when the following detailed description of the preferred embodiment is considered taken in conjunction with the appended drawings.

BEST MODE FOR CARRYING OUT THE INVENTION

Hereinbelow, an adsorbent, an adsorption apparatus, and a method for manufacturing the adsorption apparatus according to the present invention will be described in detail with reference to preferred embodiments.

Figure 1:
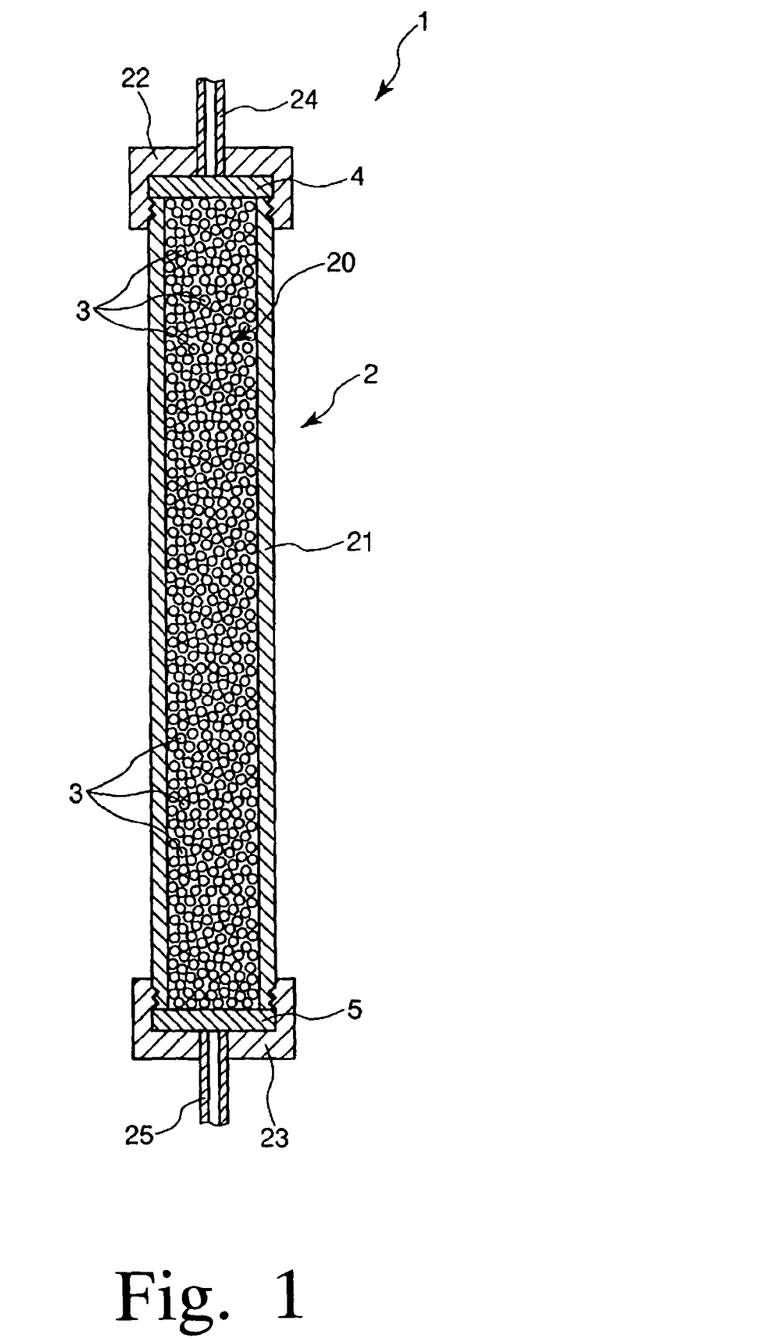
FIG. 1 is a cross-sectional view which shows an embodiment of the adsorption apparatus according to the present invention.

FIG. 1 is a cross-sectional view which shows an embodiment in which the adsorption apparatus according to the present invention uses the adsorbent according to the present invention. It is to be noted that in the following description, the upper side and the lower side in FIG. 1 will be referred to as "inflow side" and "outflow side", respectively.

Here, the "inflow side" means the side on which a liquid such as a sample or an eluant is fed into the adsorption apparatus according to the present invention for separating and purifying an object compound. On the other hand the "outflow side" means the side opposite to the "inflow side", that is, the side on which the liquid flows out of the adsorption apparatus according to the present invention.

The adsorption apparatus 1 shown in FIG. 1 includes a column 2, a particulate adsorbent 3, and two filter members 4 and 5.

The column 2 is composed of a column body 21 and caps 22 and 23 attached to the inflow side end and the outflow side end of the column body 21, respectively.

The column body 21 is formed from a hollow cylindrical member. Examples of a constituent material of each of the components (members) constituting the column 2 including the column body 21 include various glass materials, various resin materials, various metallic materials, and various ceramic materials.

The column body 21 has an opening on each of the both ends thereof, and the opening on the inflow side and the opening on the outflow side are covered with the filter members 4 and 5, respectively. In such a state, the caps 22 and 23 are threadedly attached to the inflow side end and the outflow side end of the column body 21, respectively.

The column 2 having such a structure described above has an adsorbent filling space 20 defined by the column body 21 and the filter members 4 and 5. This adsorbent filling space 20 is filled with the adsorbent 3.

The liquid-tightness of the column body 21 is ensured by attaching the caps 22 and 23 to the column body 21.

An inlet pipe 24 and an outlet pipe 25 are liquid-tightly fixed into substantially middle portions of the caps 22 and 23, respectively. Through the inlet pipe 24 and the filter member 4, a liquid such as a sample or an eluant is fed to the adsorbent 3. The liquid fed to the adsorbent 3 passes through pore spaces (gaps) between particles of the adsorbent 3, and then the liquid passes through the filter member 5 and the outlet pipe 25, and then flows out of the column 2. As a result, components (compounds) contained in the sample are separated from each other based on the difference in degree of adsorption to the adsorbent 3.

Each of the filter members 4 and 5 has the function of preventing the discharge of the adsorbent 3 from the adsorbent filling space 20, and is formed from, for example, non-woven fabrics, foams (sponge-like porous bodies having interconnected pores), woven fabrics, or meshes made of synthetic resins such as polyurethane, polyvinyl alcohol, polypropylene, polyetherpolyamide, polyethyleneterephthalate, and polybutyleneterephthalate, or meshes made of metallic materials such as stainless steel.

The adsorbent 3 according to the present invention to be filled in the adsorbent filling space 20 has the following feature described in detail below.

At least the surface and its vicinity of the adsorbent 3 according to the present invention is composed of an apatite represented by the formula $Ca_{10}(PO_4)_6((OH)_{1-x}A_x)_2$, where A represents a halogen element and $0 \leq x \leq 1$, and a phosphate group contained in the apatite is bonded to a trivalent metal ion.

In this regard, it is to be noted that a trivalent metal ion may be bonded to a phosphate group at a ratio of 1:1 (that is, an ionic bond), or binds to a plurality of phosphate groups (that is, a coordinate bond).

Such a structure makes it possible for the adsorbent 3 to specifically adsorb a compound having a portion capable of bonding with a high affinity (that is, with a high bonding force) to a trivalent metal ion.

Examples of such a compound to be specifically adsorbed (bonded) to a trivalent metal ion include compounds having a phosphate group. The phosphate group of such a compound forms a coordinate bond with a trivalent metal ion (that is, chelation), and the thus formed coordinate bond is stronger than normal adsorption (that is, than electric bond). Therefore, the adsorption apparatus 1 using the adsorbent 3 according to the present invention allows the above-described compound to be reliably adsorbed to the adsorbent 3 so that the compound is separated from other components and purified (isolated).

Although there are various compounds having a phosphate group, in particular a phosphorylated protein is adsorbed with a very high selectivity to the adsorbent 3 according to the present invention because protein itself is highly adsorptive to an apatite.

Examples of a trivalent metal ion include $Fe^{3+}$, $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, $Ac^{3+}$, $Pu^{3+}$, $Am^{3+}$, $Cm^{3+}$, $Bk^{3+}$, $Cf^{3+}$, $Cr^{3+}$, $Rh^{3+}$, $Al^{3+}$, $Ga^{3+}$, $In^{3+}$, $Tl^{3+}$, $Sb^{3+}$, and $Bi^{3+}$ and the like. These trivalent metal ions can be used singly or in combination of two or more of them. All of these trivalent metal ions are preferably used because they can exist with stability.

Among these trivalent metal ions, $Fe^{3+}$ is particularly preferable because it has a very high bonding ability to a phosphate group (that is, $Fe^{3+}$ has a very high affinity for a phosphate group). Therefore, by using $Fe^{3+}$ as a trivalent metal ion, it is possible for the adsorbent 3 to maintain its adsorption ability for a long period of time as well as to have a very high ability to specifically adsorb a compound having a phosphate group (especially, a phosphorylated protein).

Such a trivalent metal ion as described above is bonded to the apatite described above to the extent that the adsorbent 3 can appropriately exhibit the ability to specifically adsorb the compound described above. The amount of a trivalent metal ion to be bonded to the apatite is not particularly limited, but is preferably in the range of about 0.1 to 100 mg, more preferably in the range of about 0.5 to 25 mg, per gram of the apatite.

An apatite represented by the above-described compositional formula may be one in which hydroxyl groups are not substituted, but is preferably one in which at least part of the hydroxyl groups is substituted by a halogen group (that is, by a halogen element A). By doing so, it is possible to enhance the bonding force between elements (ions) constituting the apatite, thereby improving the durability of the apatite (that is, the adsorbent 3) as well as the resistance to solvents (especially, acid resistance) thereof.

The halogen element A is preferably F (that is, a fluorine element). A fluoride ion has a higher electronegativity as compared to other halide ions. Therefore, by substituting at least a part of hydroxyl groups by a fluoro group, it is possible to further enhance the effects described above.

The symbol "x" in the compositional formula described above, that is, the substitution rate of a halogen element A is not particularly limited, but it is preferred that the substitution rate is as large as possible. Specifically, the substitution rate of a halogen element A is preferably in the range of about 0.3 to 1, more preferably in the range of about 0.5 to 1. If the "x" is too small, there is a case that it is not possible to sufficiently improve the durability of the adsorbent 3 and the resistance to solvents thereof depending on, for example, the kind of halogen element A used.

Further, it is preferred that the adsorbent 3 as described above has a particulate form (or a granular form) as shown in FIG. 1, but the adsorbent 3 may have other forms such as a pellet-like form (or a small-block form) and a block form (for example, a porous body in which adjacent pores are interconnected or a honeycomb form). By allowing the adsorbent 3 to have a particulate form, it is possible to increase the surface area of the adsorbent 3, thereby further increasing the amount of the above-described compound to be adsorbed to the adsorbent 3.

The average particle size of the particles of the adsorbent 3 is not particularly limited, but is preferably in the range of about 0.5 to 100 μm, more preferably in the range of about 10 to 40 μm. By using the adsorbent 3 having such an average particle size, it is possible to allow the adsorbent 3 to have a sufficient surface area while preventing clogging of the filter member 5 reliably.

In this regard, it is to be noted that the entire of the adsorbent 3 is composed of an apatite represented by the above-described compositional formula, or otherwise only the surface and its vicinity of the adsorbent 3 is composed of an apatite represented by the above-described compositional formula.

Further, in the adsorption apparatus 1 according to the present invention, the adsorbent filling space 20 of the column 2 can be partially filled with the adsorbent 3, but it is preferred that the adsorbent filling space 20 be substantially fully filled with the adsorbent 3 as shown in FIG. 1. By doing so, it is possible to further enhance the ability to separate and purify the above-described compound as compared to an adsorption apparatus in which the adsorption filling space 20 is partially filled with the adsorbent 3 and the remaining space is filled with an adsorbent composed of hydroxyapatite.

Further, it is also preferred that all the adsorbent 3 contained in the adsorbent filling space 20 has substantially the same composition. This makes it possible for the adsorption apparatus 1 to have a particularly high ability to separate and purify the compound described above.

Such an adsorption apparatus 1 can be manufactured by, for example, a method in which a solution containing a trivalent metal ion is passed through the adsorbent filling space 20 of the column 2 filled with an apatite powder represented by the formula $Ca_{10}(PO_4)_6((OH)_{1-x}A_x)_2$, where A represents a halogen element and $0 \leq x \leq 1$.

According to such a method, it is possible to manufacture the adsorbent 3 and the adsorption apparatus 1 easily in a short period of time.

As described above, in the adsorption apparatus 1 of the present invention, it is preferred that all the adsorbent 3 contained in the adsorbent filling space 20 has substantially the same composition (in particular, it is preferred that all the adsorbent 3 have substantially the same composition throughout the adsorbent filling space 20). The use of the manufacturing method described above is advantageous since it is possible to prevent occurrence of variations in the composition of the absorbent 3.

In this method, the amount of a trivalent metal ion to be contained in 1 L of the solution described above (that is, the concentration of a trivalent metal ion in the solution) is preferably in the range of about 1 to 50 mol, more preferably in the range of about 5 to 30 mol, per mol of the apatite powder filled in the adsorbent filling space 20. If the trivalent metal ion content is too small, there is a case that the time required for allowing a trivalent metal ion to be bonded to the apatite powder becomes unnecessarily long because the amount of the solution to be used is increased. On the other hand, even if the trivalent metal ion content exceeds the above upper limit value, it cannot be expected that the amount of a trivalent metal ion to be adsorbed to the apatite powder will be further increased.

The total amount of the above-described solution to be passed through the adsorbent filing space 20 is not particularly limited, but is preferably in the range of about 1 to 50 mL, more preferably in the range of about 5 to 30 mL, in a case where the amount of a trivalent metal ion contained in the solution is within the above range. If the total amount of the above-described solution to be passed through the adsorbent filing space 20 is too small, there is a case that a trivalent metal ion is not sufficiently adsorbed to the apatite powder depending on the amount of the trivalent metal ion contained in the solution. On the other hand, even if the total amount of the above-described solution to be passed through the adsorbent filing space 20 exceeds the above upper limit value, the time required for allowing a trivalent metal ion to be bonded to the apatite powder becomes unnecessarily long and it cannot be expected that the amount of the trivalent metal ion to be adsorbed to the apatite powder will be increased in proportion to the total amount of the solution passed through the adsorbent filing space 20.

The flow rate of the solution described above is preferably in the range of about 0.1 to 10 mL/min, more preferably in the range of about 1 to 5 mL/min. If the flow rate is too low, the time required for allowing a trivalent metal ion to be bonded to the apatite powder becomes unnecessarily long. On the other hand, if the flow rate is too high, there is a case where a trivalent metal ion is not sufficiently adsorbed to the apatite powder depending on the amount of the trivalent metal ion contained in the solution.

According to such a method as described above, it is possible to control the amount of a trivalent metal ion to be bonded to the apatite powder as desired by appropriately setting the conditions of the above-described solution (that is, ion content, total amount of the solution to be passed through the adsorbent filling space, and flow rate).

In this method, the direction in which the above-described solution is passed through the adsorbent filling space 20 is not particularly limited. For example, the above-described solution is continuously or intermittently passed through the adsorbent filling space 20 in only one direction from the inflow side to the outflow side, or a given amount of the above-described solution is passed through the adsorbent filling space 20 in a direction from the inflow side to the outflow side and then a given amount of the solution is passed through the adsorbent filling space 20 in a reverse direction. In the latter case, such operation for passing the solution through the adsorbent filling space 20 can be repeated two or more times.

The above-described solution is not particularly limited as long as it contains a trivalent metal ion. Examples of such a solution include solutions of halides such as fluoride, chloride, bromide, and iodide, sulfates, nitrates, phosphates, and hydroxides.

Next, an example of usage of the adsorption apparatus according to the present invention will be described with reference to a case where a phosphorylated protein is to be separated and purified.

First, a solution is prepared as a sample by dissolving a plurality of proteins such as a phosphorylated protein and a non-phosphorylated protein in a buffer solution. Then, the sample is fed through the inlet pipe 24 and the filter member 4 to the adsorbent 3 to pass through the column 2. As a result, a component which is not adsorbed to the adsorbent 3 (that is, the non-phosphorylated protein) passes through the filter 5 and the outlet pipe 5 and then flows out of the column 2. On the other hand, a component selectively adsorbed to the adsorbent 3 (that is, the phosphorylated protein) is retained in the column 2.

Here, examples of the buffer solution to be used include phosphate buffer, Tris-HCl buffer, and Good's buffer.

Then, an eluant is fed through the inlet pipe 24 into the column 2, and then the eluant discharged from the outlet pipe 25 of the column 2 is collected.

As such an eluant, a buffer solution containing a material having a higher adsorptivity to the adsorbent 3 than that of the phosphorylated protein adsorbed to the adsorbent 3 (that is, a competitive reagent) and a chelating agent, a buffer solution having a higher salt concentration than that of the above-described buffer solution, or a buffer solution having a lower pH than that of the above-described buffer solution (about pH 5.5 to pH 10) can be used. When the eluant is fed into the column 2 (that is, when the eluant is passed through the adsorbent filling space 20), the concentration of a solute in the eluant may be changed with the lapse of time.

When the eluant comes into contact with the adsorbent 3, the phosphorylated protein selectively adsorbed to the adsorbent 3 is removed from the adsorbent 3, and is then mixed into the eluant.

The adsorbent, the adsorption apparatus, and the method for manufacturing the adsorption apparatus according to the present invention have been described above, but the present invention is not limited thereto.

EXAMPLES

Next, actual examples according to the present invention will be described.

1. Manufacture of Adsorption Apparatus

In each of the following Examples 1 and 2 and Comparative Example, five adsorption apparatuses were manufactured.

Example 1

Hydroxyapatite was synthesized by a well-known wet synthesis method to obtain a hydroxyapatite slurry.

The hydroxyapatite slurry was spray-dried to obtain a powder having an average particle size of 40 μm. Then, the powder was sintered at 700° C. for 4 hours in the atmosphere.

The hydroxyapatite powder was suspended in a 10 mM phosphate buffer solution, and an adsorbent filling space of a column (inner diameter 4 mm×length 100 mm) was filled with the suspension. Two stainless steel mesh filters having an average aperture size of 2 μm were used as filter members.

The amount of the hydroxyapatite powder (as an adsorbent) filled in the adsorbent filling space was 0.7 g (about 0.7 mmol).

Next, a 10 mM $FeCl_3$ solution was fed through an inlet pipe into the column at a flow rate of 1 mL/min for 10 minutes to allow $Fe^{3+}$ to be bonded to a phosphate group contained in the hydroxyapatite powder. In this way, an adsorbent was obtained and adsorption apparatuses were manufactured.

Here, the degree of bonding of $Fe^{3+}$ to a phosphate group contained in the hydroxyapatite powder was evaluated in the following manner.

Specifically, in the step of allowing $Fe^{3+}$ to be bonded to a phosphate group contained in the hydroxyapatite powder, the $FeCl_3$ solution discharged from an outlet pipe was fractionated every 1 minute, and Fe concentration of each of the fractions was measured.

Next, a 10 mM phosphate buffer solution as a washing solution was fed through the inlet pipe into the column to wash the adsorbent. After it was confirmed that no Fe was eluted from the column, a 10 mM $FeCl_3$ solution was again fed into the column at a flow rate of 1 mL/min for 10 minutes, and the $FeCl_3$ solution discharged from the outlet pipe was fractionated every 1 minute to measure the Fe concentration of each of the fractions.

It is to be noted that the Fe concentration was measured by an atomic absorption method using an atomic absorption spectrometer ("AA-6200", manufactured by Shimadzu Corporation).

Figure 2:
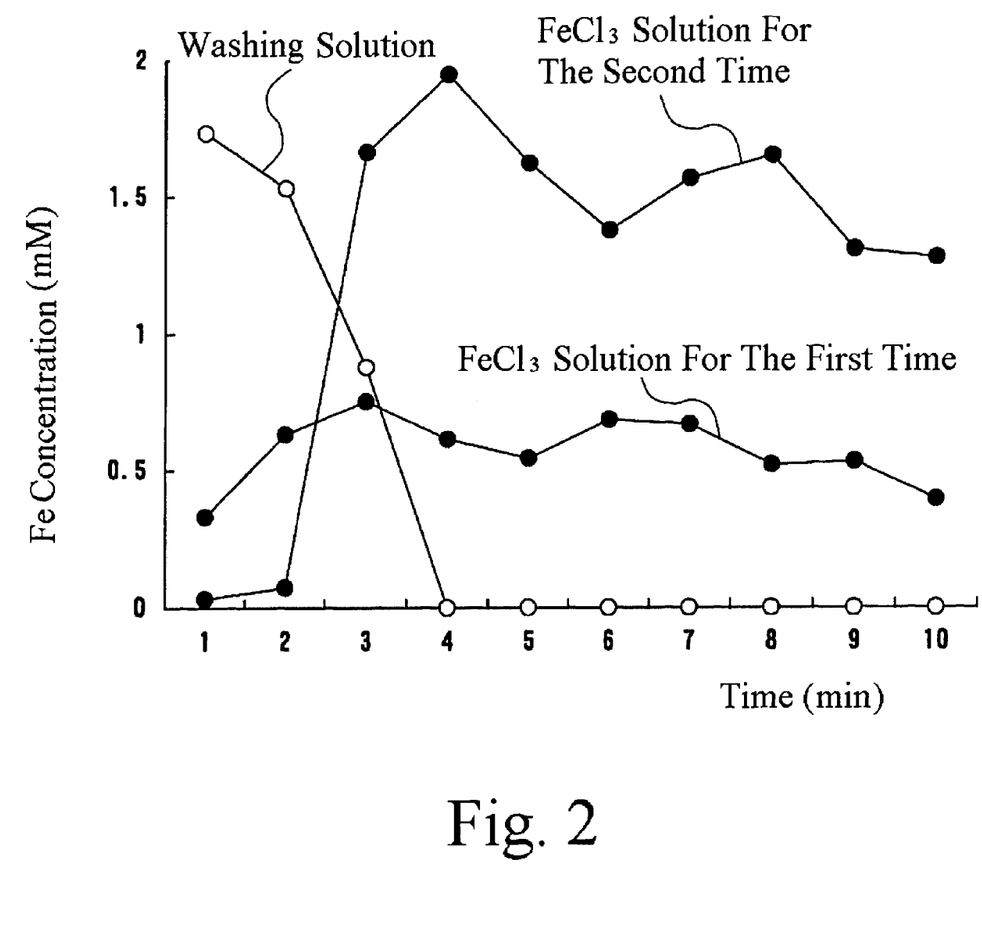
FIG. 2 is a graph which shows the change of the Fe concentration in each of the fractions of the $FeCl_3$ solution fractionated when the degree of bonding of $Fe^{3+}$ to a phosphate group contained in the hydroxyapatite powder was evaluated in the Example 1.

FIG. 2 shows the measurement result of the Fe concentration in each of the fractions of the $FeCl_3$ solution fractionated during the step of passing the $FeCl_3$ solution through the column twice. FIG. 2 also shows the measurement result of the Fe concentration in the washing solution discharged from the column.

As shown in FIG. 2, the Fe concentration in the $FeCl_3$ solution discharged from the column during the step of passing the $FeCl_3$ solution through the column for the second time was higher than the first time. The reason for this is supposed to be that $Fe^{3+}$ is bonded to a phosphate group contained in the hydroxyapatite powder during the step of passing the $FeCl_3$ solution through the column for the first time so that the number of phosphate groups capable of bonding to $Fe^{3+}$ is decreased in the step of passing the $FeCl_3$ solution through the column for the second time.

This result suggests that $Fe^{3+}$ can be easily bonded to a phosphate group on the surface of the hydroxyapatite powder by passing the $FeCl_3$ solution through the column.

Further, the amount of Fe in the powder was measured using an atomic absorption spectrometer ("AA-6200", manufactured by Shimadzu Corporation), and as a result it was found that 2.9 mg of $Fe^{3+}$ was bonded per gram of the adsorbent.

Example 2

Fluorapatite $(Ca_{10}(PO_4)_6((OH)_{0.7}F_{0.3})_2)$ was synthesized by a well-known wet synthesis method to obtain a fluorapatite slurry.

The fluorapatite slurry was spray-dried to obtain a powder having an average particle size of 40 μm. Then, the powder was sintered at 700° C. for 4 hours in the atmosphere.

Adsorption apparatuses were manufactured in the same manner as in the Example 1 except that 1 g (about 1 mmol) of the fluorapatite powder was used as an adsorbent instead of the hydroxyapatite powder.

According to the elemental analysis method described in the Example 1, the amount of Fe in the powder was measured, and as a result it was found that 2.9 mg of $Fe^{3+}$ was bonded per gram of the adsorbent.

Comparative Example

Adsorption apparatuses were manufactured in the same manner as in the Example 1 except that the step of passing the $FeCl_3$ solution through the column was omitted.
2. Evaluation
2-1 Adsorption Characteristics of Phosphorylated Protein Evaluation of adsorption characteristics of a phosphorylated protein was performed on the adsorption apparatuses manufactured in the Example 2 and the Comparative Example in the following manner.

First, the solution filled in the column of each of the adsorption apparatuses was replaced with a 10 mM phosphate buffer solution (pH 6.8).

Then, ovalbumin which was not phosphorylated (hereinafter, referred to as a "non-phosphorylated ovalbumin) and ovalbumin containing one or two phosphate groups (hereinafter, referred to as a "phosphorylated ovalbumin) were dissolved in the same phosphate buffer solution as described above so that the concentration of each of the ovalbumins was 50 mg/mL, and 2 mL of the thus obtained sample was fed into the column to pass through the column.

Then, the two types of ovalbumin were eluted with an increasing gradient of 10 mM to 300 mM phosphate buffer solution in 15 minutes. In this regard, it is to be noted that the flow rate of the phosphate buffer solution was 1 mL/min. The time that elapsed before each of the two types of ovalbumin started to elute from the column (hereinafter, also referred to as "retention time") was measured (determined) using a UV monitor at 280 nm.

The measurement results are shown in the following Table 1. It is to be noted that each of the values in Table 1 is the average of values measured using the five adsorption apparatuses of the Example 2 or the Comparative Example.

TABLE 1

| | Retention time | |
|---|---|---|
| | Phosphorylated ovalbumin | Non-phosphorylated ovalbumin |
| Example 2 | 5 min and 40 sec | 1 min and 30 sec |
| Comparative Example | 5 min and 20 sec | 4 min and 30 sec |

As shown in Table 1, the time that elapsed before the non-phosphorylated ovalbumin started to elute from the column of the adsorption apparatus of the Example 2 was clearly shorter than that of the adsorption apparatus of the Comparative Example.

Specifically, in the case of the adsorption apparatus of the Example 2, the degree of separation between the phosphorylated protein and the non-phosphorylated protein was higher as compared to the case of the adsorption apparatus of the Comparative Example.

Further, the phosphate buffer solution collected from the adsorption apparatus of the Example 2 contained almost no $Fe^{3+}$.
2-2 Separation Characteristics of Phosphorylated Protein Evaluation of the separation characteristics of a phosphorylated protein was performed on the adsorption apparatuses manufactured in the Example 1 and the Comparative Example in the following manner.

The adsorption apparatus of the Example 1 or the Comparative Example was installed in a high-performance liquid chromatography system ("Duo-flow", manufactured by Bio-Rad), and the solution filled in the column was replaced with a 1 mM Tris-HCl buffer solution (pH 7.8).

Then, ovalbumin (manufactured by Sigma) was dissolved in the same Tris-HCl buffer solution as described above so that the concentration of the ovalbumin was 5 mg/mL to prepare a sample solution. It is to be noted that the ovalbumin was a mixture of phosphorylated ovalbumin and non-phosphorylated ovalbumin.

Then, 50 μL of the sample solution was injected into the HPLC system. An eluant was a mixture of the Tris-HCl buffer solution and a 10 mM sodium phosphate buffer solution, and the mixing ratio between the Tris-HCl buffer solution and the 10 mM sodium phosphate buffer solution was changed with time from 100:0 to 0:100 in 15 minutes. The flow rate of the eluant was 1 mL/min.

The elution pattern of the ovalbumin into the eluant discharged from the column was determined.

Figure 3:
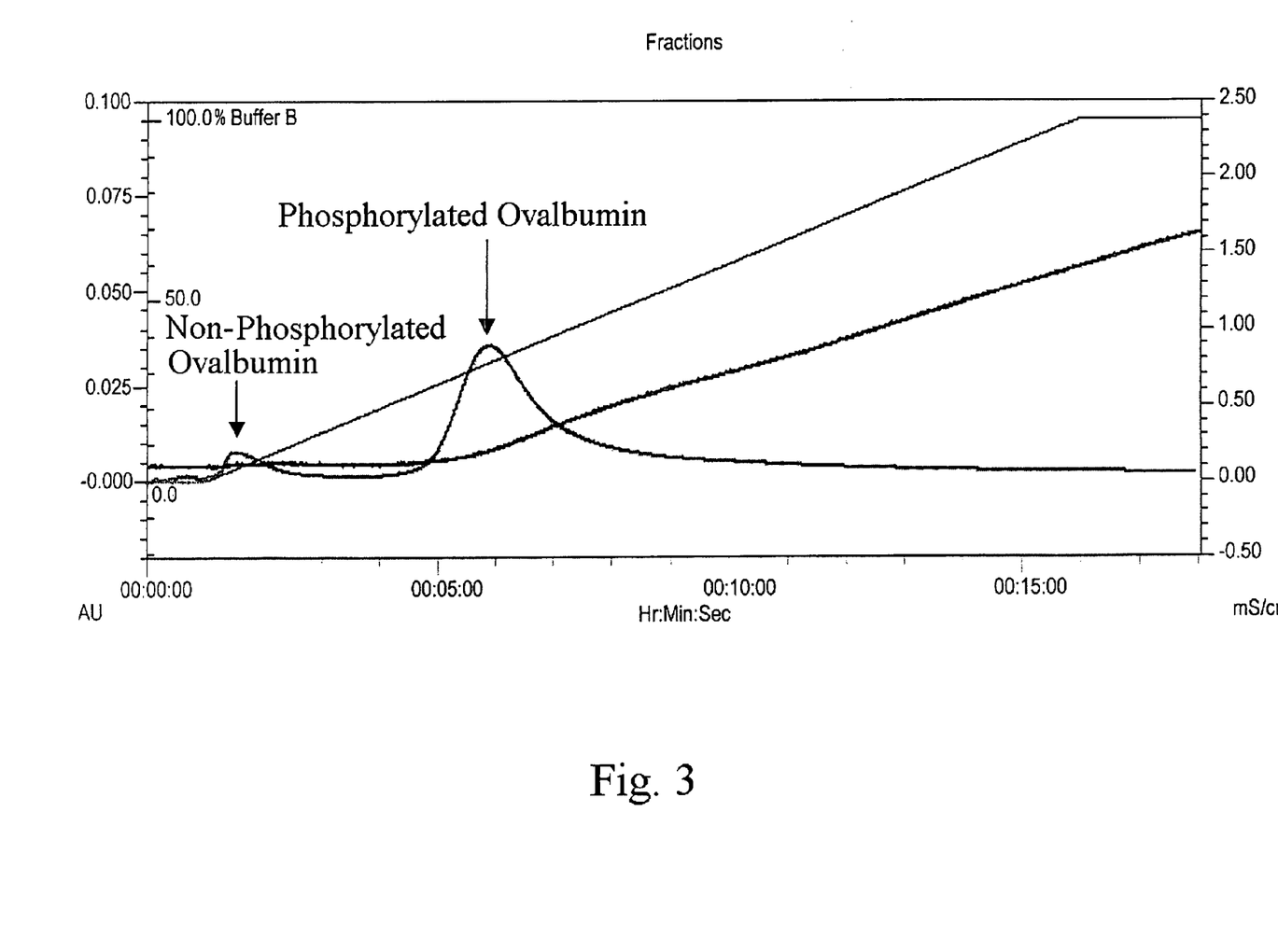
FIG. 3 is a graph which shows the elution pattern of the ovalbumin in the case of the adsorption apparatus of the Example 1.
Figure 4:
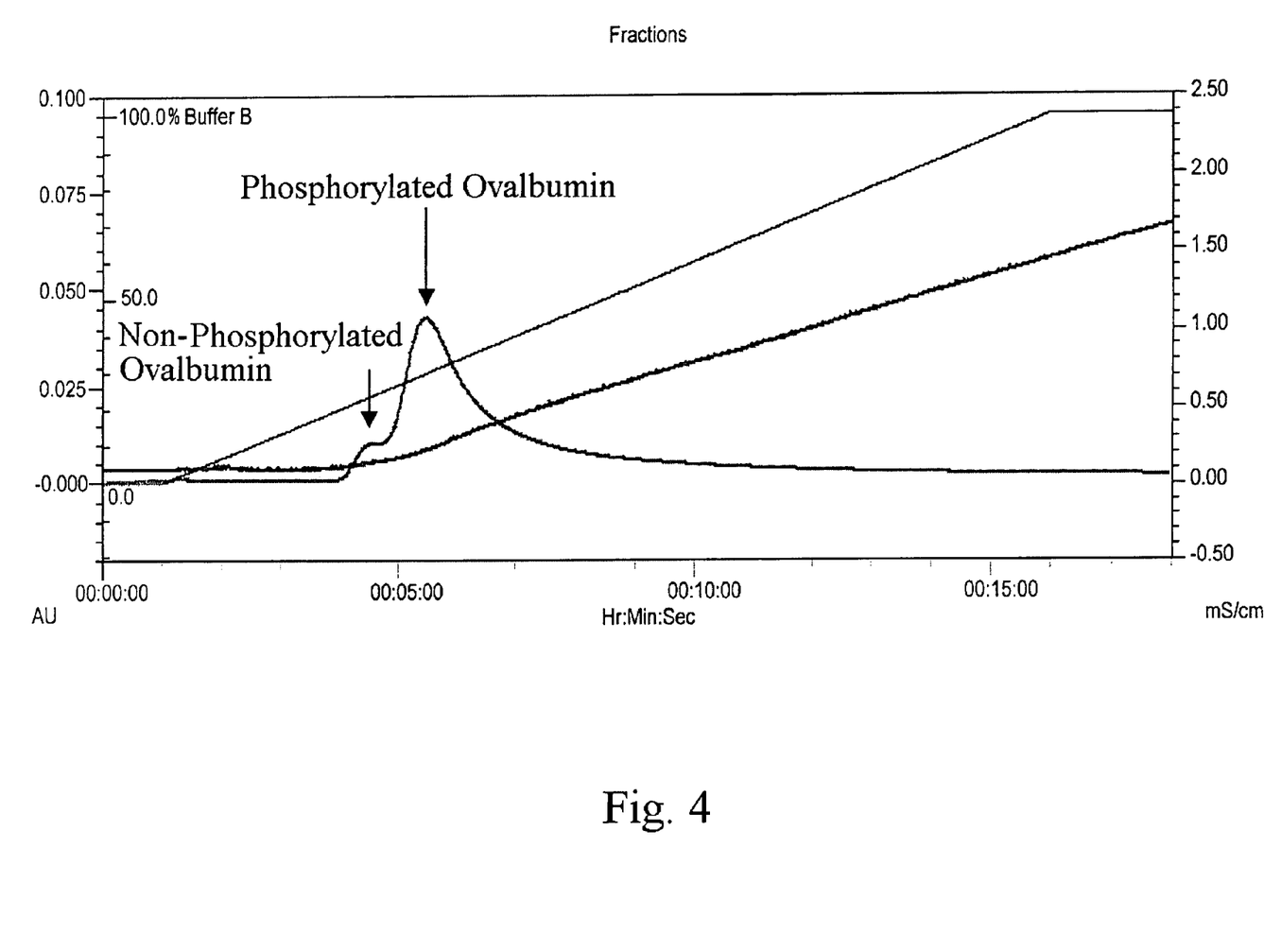
FIG. 4 is a graph which shows the elution pattern of the ovalbumin in the case of the adsorption apparatus of the Comparative Example.

FIG. 3 shows the elution pattern of the ovalbumin in the case of the adsorption apparatus of the Example 1, and FIG. 4 shows the elution pattern of the ovalbumin in the case of the adsorption apparatus of the Comparative Example.

As shown in FIG. 3, in the case of the adsorption apparatus of the Example 1, the phosphorylated ovalbumin was specifically adsorbed to the adsorbent, but the non-phosphorylated ovalbumin was eluted from the column at an early stage.

On the other hand, in the case of the adsorption apparatus of the Comparative Example, as shown in FIG. 4, the ovalbumin containing a phosphate group and the ovalbumin containing no phosphate group were not clearly separated from one another, that is, the ovalbumin was non-specifically adsorbed to the adsorbent irrespective of the presence or absence of a phosphate group.

In this regard, it is to be noted that the adsorption apparatus of the Example 2 provided the same elution pattern as the adsorption apparatus of the Example 1.

As has been described above, the adsorption apparatus of each of the Examples 1 and 2 (that is, the adsorption apparatus according to the present invention) has an excellent ability to specifically adsorb phosphorylated ovalbumin (that is, a phosphorylated protein) and therefore can be suitably used for separation and purification of a phosphorylated protein.

INDUSTRIAL APPLICABILITY

As described above, by allowing a trivalent metal ion to be bonded to a phosphate group contained in an apatite according to the present invention, it is possible to collect a highly-pure compound having an affinity for the trivalent metal ion (that is, an object compound) in good yield.

Further, by appropriately selecting a trivalent metal ion, it is possible to select the kind of object compound to be separated and purified. For example, in a case where $Fe^{3+}$ is used as a trivalent metal ion, the ability to specifically adsorb a compound having a phosphate group, such as a phosphorylated protein is enhanced.

Finally, it is to be noted that this application is based upon Japanese Patent Application No. 2003-164336, the entire disclosure of which is incorporated herein by reference.

What is claimed is:

1. A method for manufacturing an adsorption apparatus, the adsorption apparatus comprising a column having an adsorbent filling space, and an adsorbent filled into the adsorbent filling space of the column, wherein the adsorbent comprises a plurality of apatite particles, each having a surface, and each comprising an apatite represented by the formula $Ca_{10}(PO_4)_6((OH)_{1-x}A_x)_2$, where A represents a halogen element and $0.3 \leq x \leq 1$, and $Fe^{3+}$ bonded to a phosphate group contained in the apatite forming the surface of each of the apatite particles, and wherein average particle size of the apatite particles is in the range of 0.5 to 100 μm and the amount of the $Fe^{3+}$ to be bonded to the apatite forming the surface of each of the apatite particles is in the range of 0.1 to 100 mg per gram of the apatite, the method comprising:
preparing the column in which the adsorbent filling space is filled with said apatite particles; and
passing a solution containing $Fe^{3+}$ through the adsorbent filling space of the column at a flow rate of 0.1 to 10 ml/min so that the $Fe^{3+}$ is selectively bonded to the phosphate group contained in the apatite forming the surface of each of the apatite particles so as to obtain said adsorbent.

2. The method for manufacturing an adsorption apparatus as claimed in claim 1, wherein the amount of the $Fe^{3+}$ contained in 1 L of the solution is in the range of 1 to 50 mol per 1 mol of the apatite.

3. The method for manufacturing an adsorption apparatus as claimed in claim 1, wherein the total amount of the solution containing the $Fe^{3+}$ to be passed through the adsorbent filling space is in the range of 1 to 50 mL.

4. The method for manufacturing an adsorption apparatus as claimed in claim 1, wherein the solution comprises $FeCl_3$.

5. The method for manufacturing an adsorption apparatus as claimed in claim 1, wherein the A is a fluorine element.

6. The method for manufacturing an adsorption apparatus as claimed in claim 1, wherein the adsorbent filling space is substantially fully filled with the adsorbent.

7. The method for manufacturing an adsorption apparatus as claimed in claim 1, wherein all the adsorbent contained in the adsorbent filling space has substantially the same composition.

8. An adsorbent capable of adsorbing a phosphorylated protein, the adsorbent comprising a plurality of apatite particles each having a surface and each comprising an apatite represented by the formula $Ca_{10}(PO_4)_6((OH)_{1-x}A_x)_2$, where A represents a halogen element and $0.3 \leq x \leq 1$, and $Fe^{3+}$ bonded to a phosphate group contained in the apatite forming the surface of each of the apatite particles, and wherein average particle size of the apatite particles is in the range of 0.5 to 100 μm and the amount of the $Fe^{3+}$ to be bonded to the apatite forming the surface of each of the apatite particles is in the range of 0.1 to 100 mg per gram of the apatite.

9. The adsorbent as claimed in claim 8, wherein the A is a fluorine element.

* * * * *